ABOVE

United States Patent
Petcavich

(10) Patent No.: US 11,054,408 B2
(45) Date of Patent: Jul. 6, 2021

(54) PROJECTED CAPACITIVE MULTI ELECTRODE EUKARYOTIC CELL ARRAY

(71) Applicant: StemoniX Inc., Eden Prarie, MN (US)

(72) Inventor: Robert John Petcavich, The Woodlands, TX (US)

(73) Assignee: StemoniX Inc., Eden Prairie, MN (US)

( * ) Notice: Subject to any disclaimer, the term of this patent is extended or adjusted under 35 U.S.C. 154(b) by 0 days.

(21) Appl. No.: 15/588,154

(22) Filed: May 5, 2017

(65) Prior Publication Data
US 2017/0322194 A1     Nov. 9, 2017

Related U.S. Application Data

(60) Provisional application No. 62/333,111, filed on May 6, 2016.

(51) Int. Cl.
    *G01N 33/483*      (2006.01)
    *G01N 27/22*      (2006.01)

(52) U.S. Cl.
    CPC ......... *G01N 33/4836* (2013.01); *G01N 27/22* (2013.01)

(58) Field of Classification Search
    CPC ............ G01N 33/4836; G01N 33/2722
    USPC ............................................. 435/29
    See application file for complete search history.

(56) References Cited

U.S. PATENT DOCUMENTS

2005/0153425 A1*   7/2005   Xu .................. C12M 25/08
                                                                        435/287.1
2010/0120626 A1*   5/2010   Ross ................ C12N 13/00
                                                                        506/7

OTHER PUBLICATIONS

West, Why a Touchscreen PC Should be Your Next Workstation, PCWorld, Nov. 12, 1011, Available online at: www.pcworld.com/article/243666/why_a_touchscreen_pc_should_be_your_next_workstation.html.*
Bozkurt, Alper, et al., "Low-cost flexible printed circuit technology based microelectrode array for extracellular stimulation of the invertebrate locomotory system", Sensors and Actuators A: Physical, 169, (2011), 89-97.

* cited by examiner

*Primary Examiner* — Jennifer M. H. Tichy
(74) *Attorney, Agent, or Firm* — Schwegman Lundberg & Woessner, P.A.

(57) ABSTRACT

The present subject matter discloses various exemplary projective capacitive micro structured electrode arrays for measuring the impedance and action potential of living cells in particular induced pluripotent stem cells that are subsequently differentiated into cardiomyocytes and neurons. In one exemplary system a projective capacitive electrode array with cardiomyocytes attached onto the electrodes is formed and electrical measurements of live cell responses when exposed to external stimulants, such as small molecule drugs or biologically active compounds is recorded.

11 Claims, 6 Drawing Sheets

Self capacitance

Mutual Capacitance

Mutual Capacitive Electrode Design

Self Capacitive Electrode Design

Exemplary Electrode Design

30

Microwell Plate Attached to an Electrode Array

PROJECTED CAPACITIVE MULTI ELECTRODE EUKARYOTIC CELL ARRAY

CLAIM OF PRIORITY

This application claims the benefit of priority of U.S. Provisional Patent No. 62/333,111 filed May 6, 2016, the entire disclosure of which is incorporated by reference herein.

FIELD OF THE INVENTION

The present subject matter relates to methods and apparatus for measurement of living cell electrophysiology.

BACKGROUND

Projected Capacitive Technology (PCT) is fast becoming one of the most prevalent touch technologies for an expanding variety of applications ranging from consumer devices to commercial applications in retail, gaming and signage. Driven by the increasing number of users of touch-enabled mobile devices, consumer and professional expectations for touch applications have moved far beyond single touch requirements into the realm of multi-touch and multi-user capabilities. This disclosure will describe "projected capacitive technology" using two sensing methods, "self capacitance" and "mutual capacitance." It will also describe some exemplary different options related to these sensing methods. Each of these sensing methods may address different needs and understanding their strengths and capabilities can help hardware and software developers choose the appropriate touch technology for their application.

Projected capacitive technologies detect touch by measuring the capacitance at each addressable electrode. When a finger or a conductive stylus approaches an electrode, it disturbs the electromagnetic field and alters the capacitance. This change in capacitance can be measured by the electronics and then converted into X, Y locations that the system can use to detect touch. There are two main types of sensing methods, self-capacitance (e.g., FIG. 1) and mutual capacitance (e.g., FIG. 2), where each has its own advantages and disadvantages.

In a first implementation, the electronics measure the current on each electrode to ground and therefore this implementation is called "self-capacitance." FIG. 1 demonstrates how "self-capacitance" works. There are two options for how the system can detect touch multi-pad construction or rows and columns. In a multi-pad construction, each electrode, or "pad", is individually addressable by the electronics requiring an individual connection between the electrode and the controller. This allows multi-pad self-capacitance to support greater than one touch, but given that each pad must be individually addressed, it makes the implementation of this solution for screens greater than 3.5 inches very challenging. In a row-and-column construction, each row and column is an electrode and therefore is individually addressed by the controller. Even though the intersection of a row and column represents a unique coordinate pair, the electronics are not able to measure each individual intersection as they can only measure each electrode. This limits row and column self-capacitance implementations to single and dual touch detection where "ghost" points can be a problem. Ghost points are the result of imaginary or false row and column intersections in locations other than the touch location.

To sense touch in a self-capacitance implementation, the electronics scan through each electrode and measures the amount of current on each electrode to establish a steady-state current. When a finger or grounded conductive stylus approaches the screen, they couple to the electrodes and increase the current draw as it creates a path to ground. By determining which row and column is closest to the touch location, and using interpolation for higher precision, a controller can determine the location of a touch. Upon reading and understanding the present subject matter, other calculation methods may be employed which do not depart from the scope of the present subject matter. It is understood that the controller may be embodied in hardware, software, firmware, or combinations thereof without departing from the scope of the present disclosure.

Mutual capacitance is the intentional or unintentional capacitance between two "charge holding objects." FIG. 2 demonstrates how mutual capacitance works. Projected capacitance touchscreens intentionally create mutual capacitance between elements of columns and rows in the vicinity where each intersect the other. This allows the system electronics to measure each node (intersection) individually to detect multiple touches on the screen during one screen scan.

When a finger touches near an intersection, some of the mutual capacitance between the row and column is coupled to the finger, which reduces the capacitance at the intersection as measured by the system electronics. This reduced capacitance crosses the "touch threshold" set by the electronics indicating a touch has occurred. The present subject matter demonstrates, among other things, using projective capacitance as a method to measure electrophysiology versus touch to characterize mammalian cells that are attached to the sensing electrodes.

SUMMARY

Described herein are various exemplary techniques for using projective capacitive technology as micro structured electrodes for the measurement of both impedance and action potentials of living cells in particular cardiomyocytes and neurons derived from induced pluripotent mammalian stem cells (iPScs). In one embodiment, an 8×12 array of electrodes are adhesively bonded to a 96 well microplate to form a liquid seal. Cardiomyocytes cells are seeded onto the gold micro structured electrodes and allowed to attach and incubate at 37° C. for several days. The electrophysiology of the cells is monitored in real time and saved as a baseline measurement. The living cells can then be exposed to various drug challenges and one can measure the electrophysiology changes in real time such as impedance and action potentials and observe the cells response to the drug exposure.

This Summary is an overview of some of the exemplary teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

The following disclosure is directed towards various embodiments of the present subject matter. Although one or more of these embodiments may be preferred, the embodiments disclosed should not be interpreted, or otherwise used, as a limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The preferred embodiments of the present disclosure are directed to using projective capacitive electrode technology in combination with living cells in particular iPSc and cells differentiated from those types of stem cells. Exemplary embodiments involve forming the projective capacitive electrode array, attaching a molded array microplate to the electrode array, filling the microplate with living cells and support growth media, incubating the cells at conditions (which conditions may be well known in the art) to allow attachment and functioning, and then measuring the electrical properties of the cells attached to the electrode array such as impedance, capacitance, action potential, voltages, and current or otherwise known as cell electrophysiology.

Figure 1:
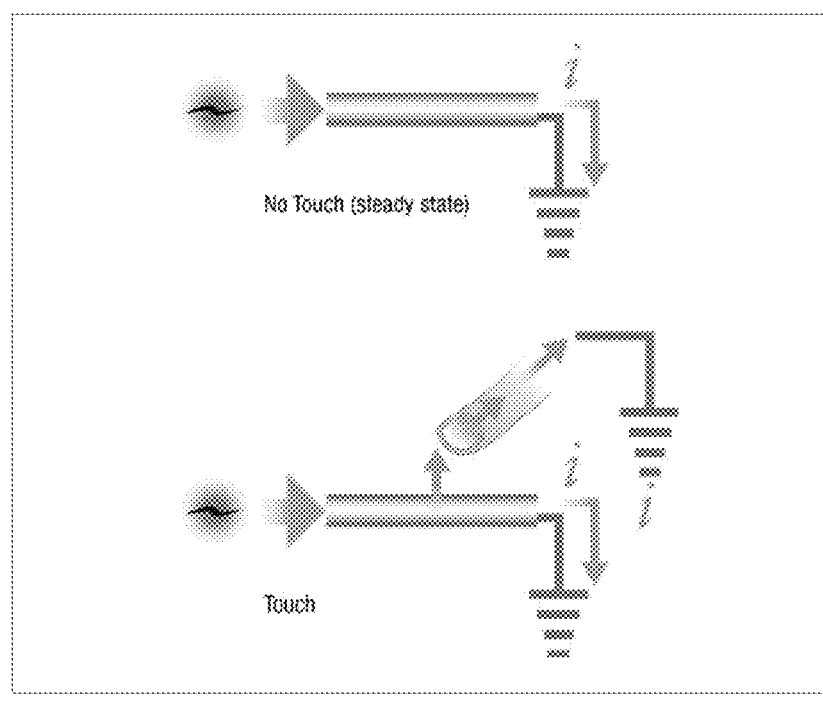
FIG. 1 shows how self-capacitance works.
Figure 2:
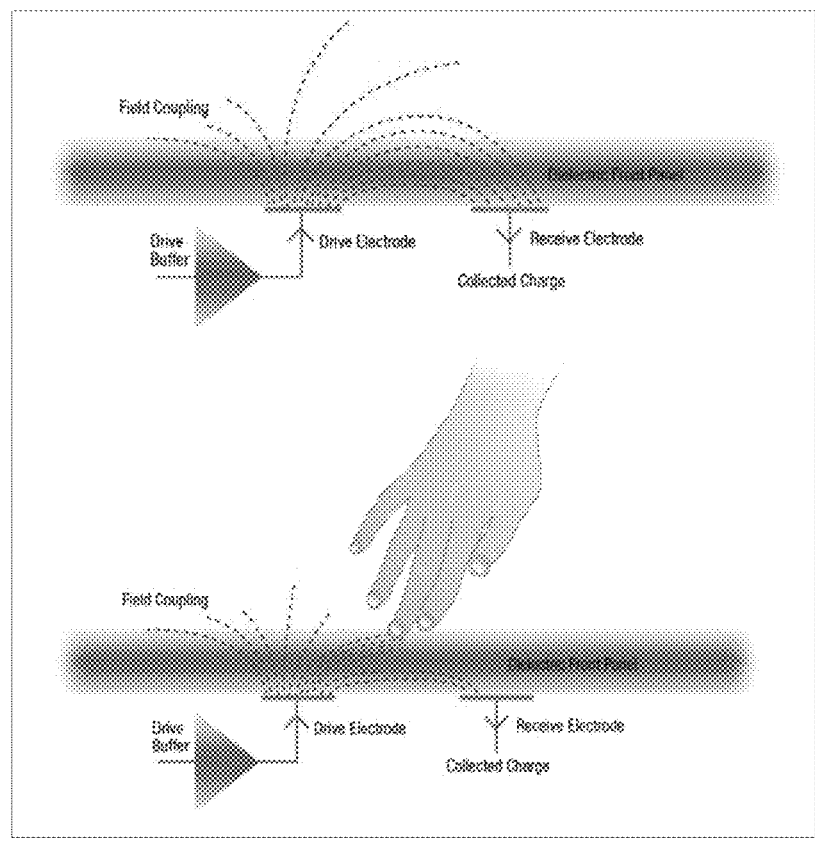
FIG. 2 shows how mutual capacitance works.
Figure 3:
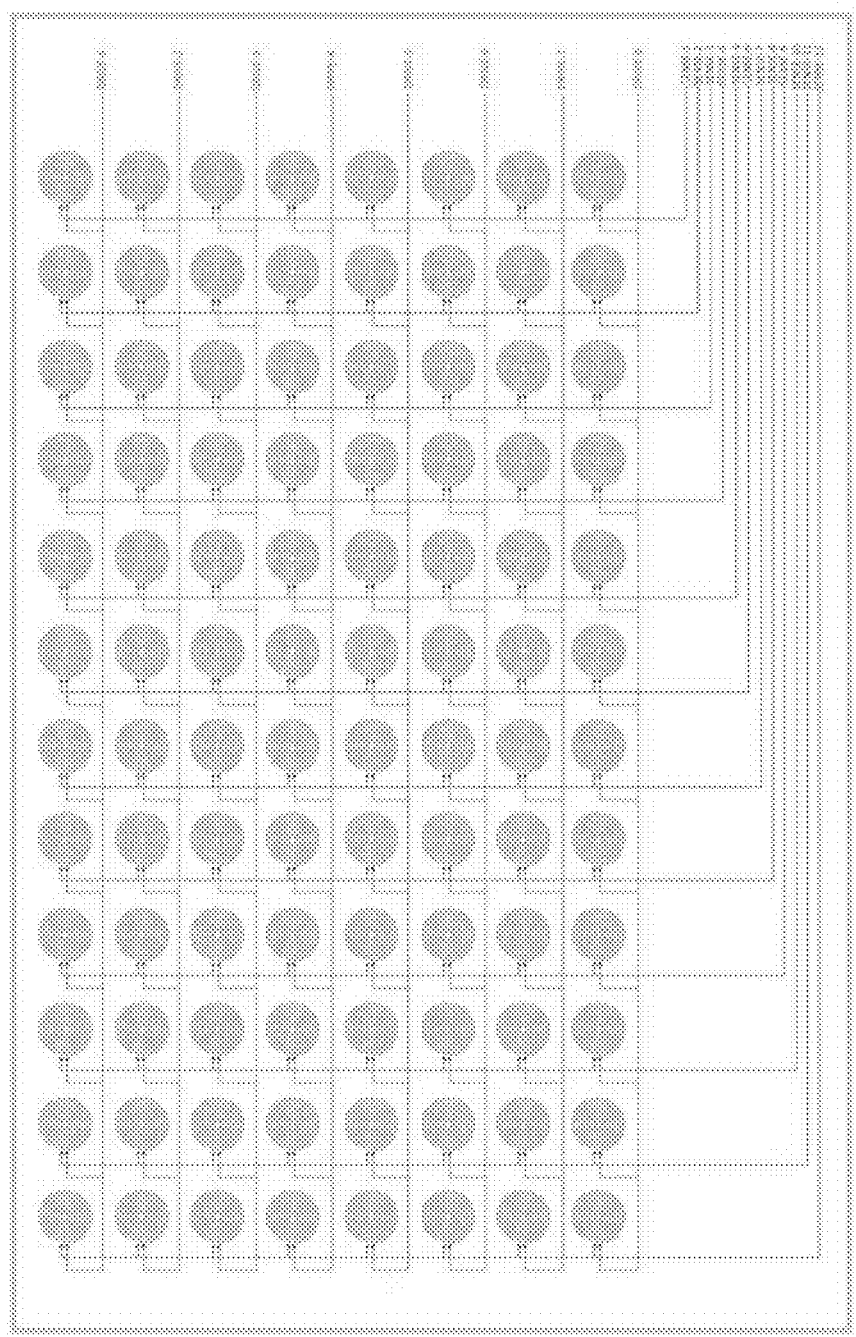
FIG. 3 shows a mutual capacitance electrode design according to one embodiment of the present disclosure.

FIG. 3 shows a mutual capacitance electrode design according to one embodiment of the present disclosure. The electrode array can be fabricated using a variety of techniques, including, but not limited to fabrication on a printed circuit board. The substrate onto which the electrode patterned is formed can be a standard PCB board well known in the art, or polymeric film such as Kapton or transparent polyester film. The thickness of the substrate can range, depending on the application. In many circumstances it is desirable to have a transparent substrate so that the investigator can perform optical measurement techniques to characterize the living cells. In that case, transparent films such as polyester, polycarbonate, cellulosic, or cyclic polyolefins may be used.

Figure 4:
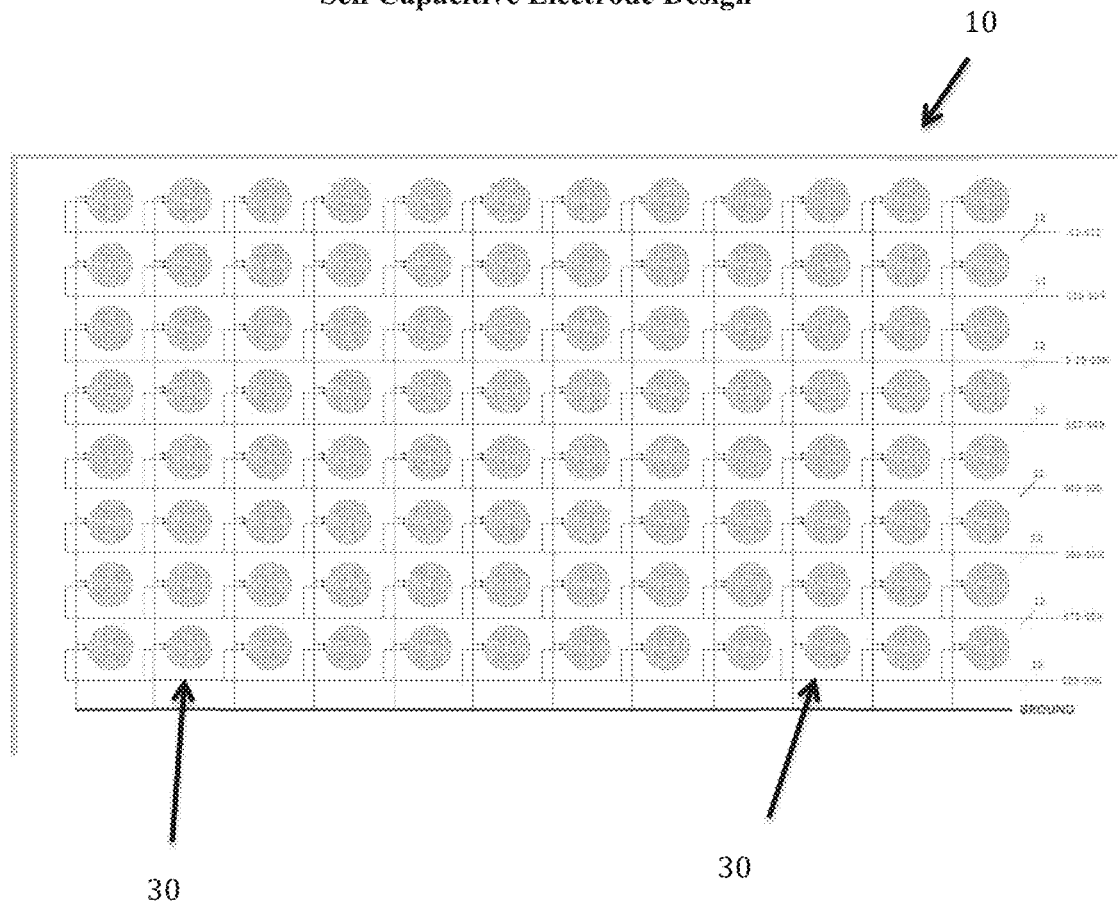
FIG. 4 shows a self-capacitive electrode design according to a preferred embodiment of the present disclosure.

FIG. 4 shows a diagram of the preferred electrode design using self-capacitance of the present invention. In various embodiments, the electrode array 10 is fabricated onto a printed circuit board. The substrate 20 onto which the electrode patterned is formed can be a standard PCB board well known in the art, or polymeric film such as Kapton or transparent polyester film. The thickness of the substrate 20 can range from 25 microns to 2 millimeters depending on the application. In many circumstances it is desirable to have a transparent substrate 20 so that the investigator can use both electrophysiology and optical measurement techniques to characterize the living cells. In that case transparent films such as polyester, polycarbonate, cellulosic, or cyclic polyolefins are preferred. Self-capacitance electrode design is preferred because it is more sensitive to measuring minute changes is capacitance and resistance.

Figure 5:
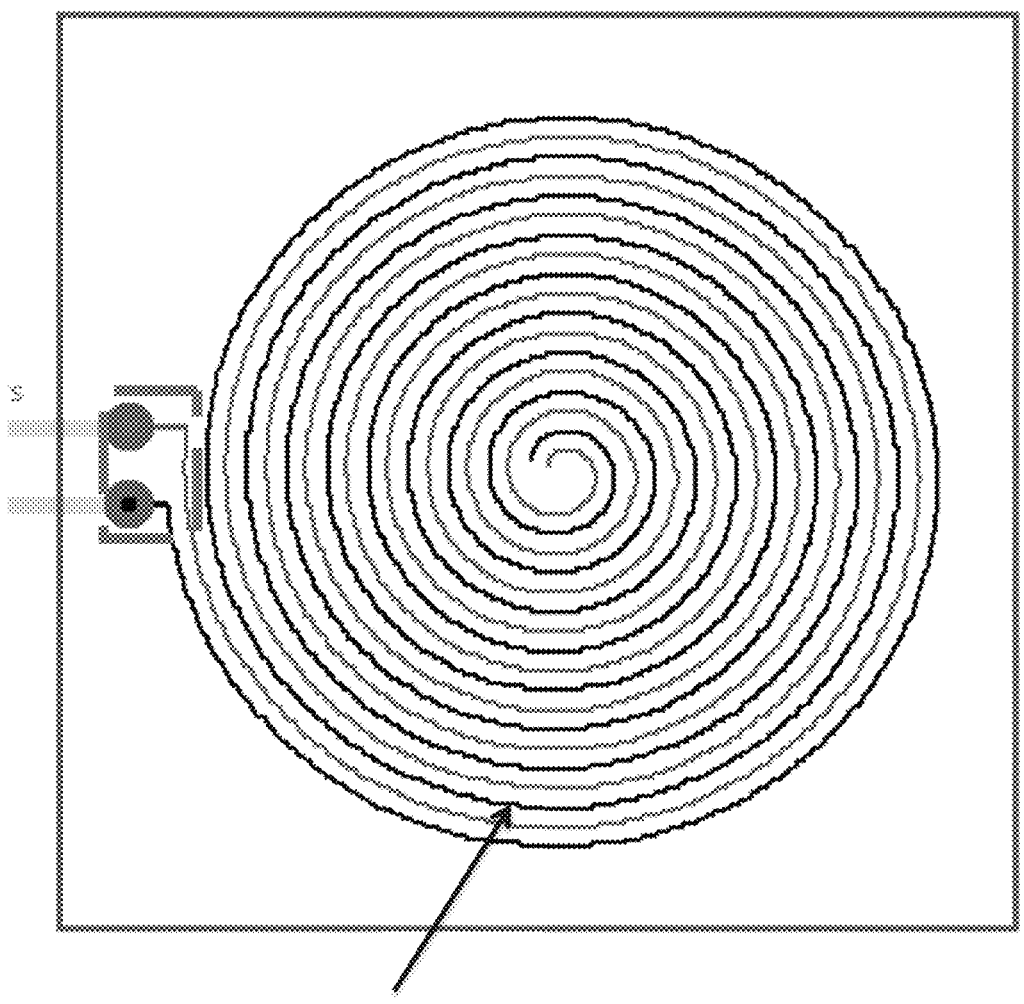
FIG. 5 shows a typical electrode design according to one embodiment of the present disclosure.

The individual electrodes 30, as demonstrated by the electrode design of FIG. 5, are located in each microplate well and in various embodiments are formed of copper traces that are subsequently gold plated for biocompatibility. The electrodes can be any geometric shapes such as inter digitated lines, squares or circles as shown in the present disclosure. In the self-capacitive configuration there is a common ground for all wells. The line widths and line spacing are critical for both electrical sensitivity and cell alignment during attachment to the gold surface. The space/trace dimensions can vary from 500 microns (u)×500 microns down to 5 microns×5 microns or any combination of the aforementioned dimensions. In the preferred embodiment 50 u×50 u, 75 u×75 u and 100 u×100 u conductive line and space is utilized.

Figure 6:
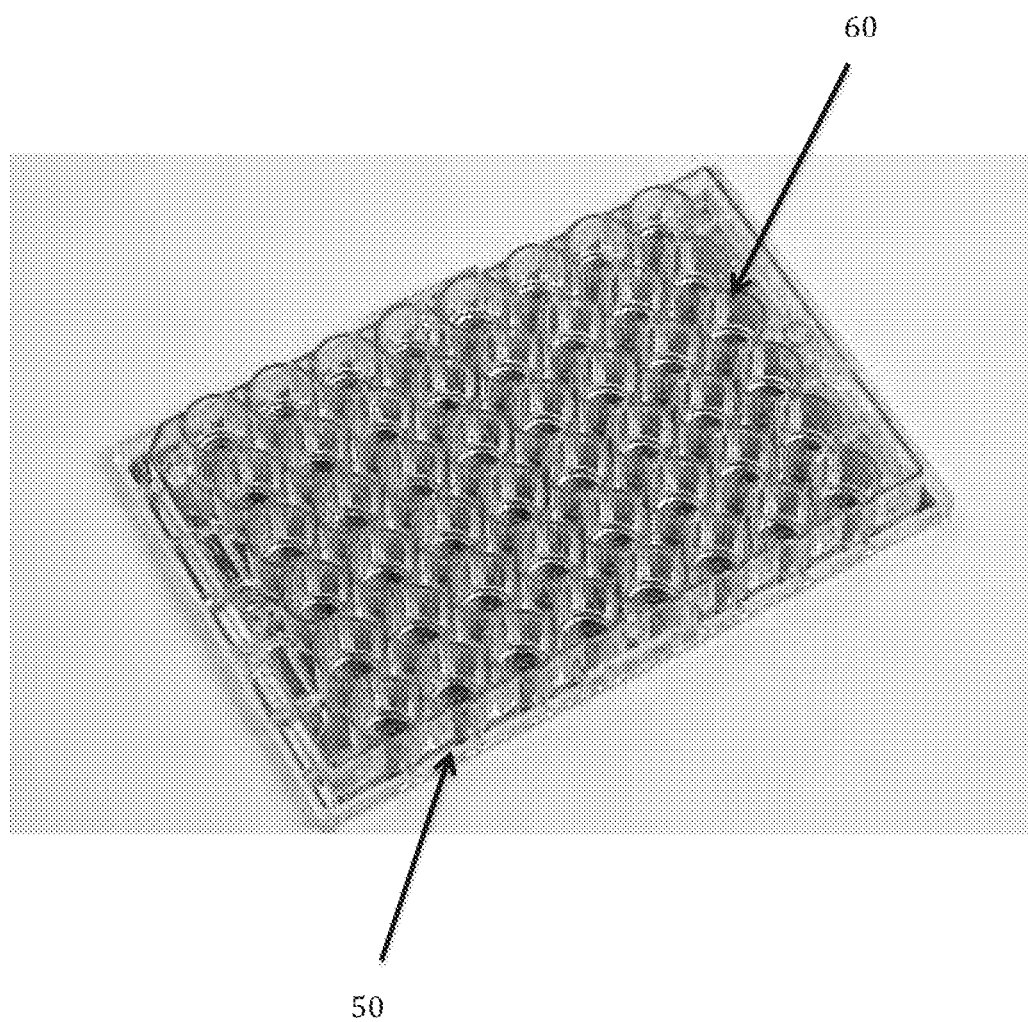
FIG. 6 shows an electrode array attached to a micro plate for cell confinement according to one embodiment of the present disclosure.

Once the electrodes are formed a microwell plate 50 as shown in FIG. 6 is attached to the patterned substrate via waterproof pressure sensitive adhesive. The microwell electrode combination is then attached to a microcontroller that scans each well to determine the electrical characteristics of the electrode pattern. Standard off the shelf touch screen microcontrollers available from Microchip, Atmel, or Cypress Semiconductor can be used in the present subject matter. It is also understood that specialized controllers may be used in various embodiments. The microwell electrode device is then electrically tested, and nutrient media added to support cell attachment and growth on the gold electrodes, is loaded into the wells 60. The amount of media that goes into each well will vary depending on the array size. The array size of the present disclosure can vary from n×n where n=1 to 100. With 96, 384 and 1536 well arrays being preferred. In the present exemplary embodiments a 96 well plate electrode array is used and the media in each well can vary from 1 microliter to 1 milliliter. Into each well is loaded the cells of interest. Prior to loading cells into the microplate electrode array a baseline electrical measurement is made of that configuration with nutrient media, which will be subsequently used to analyze the cell electrophysiology.

The number of cells loaded into each well can also vary depending on the size of the well array. There can be as few as 10 cells up to 500,000 cells per well. In the present subject matter 10,000 to 20,000 cells per well is preferred. After the cells are loaded and allowed to attach to the gold surface real time electrical measurements can be made in each well. As the cells attach and grow the electrical characteristics of the individual electrodes will change with time. For example, the impedance or electrical resistance will increase as more cells become attached or grow closer together. Alternatively, if the cells die and shrink the resistance will decrease. By knowing the resistance and capacitance other electrical properties can also be measured such a voltage, electrical potential, and also current. All the aforementioned electrical characteristics are important in analyzing cell response to drug interactions and challenges. By knowing the baseline electrical performance with growth media only in the wells that data can be subtracted from the data captured from live cells in the wells to show what electrical changes the cells are experiencing on the electrode surface.

Some exemplary embodiments include, but are not limited to a projective capacitive electrode array for measurement of living cell electrophysiology. In various embodiments, the measurement is in real-time. In various embodiments the array is fabricated onto a printed circuit board. In various embodiments the printed circuit board is a transparent material. In various embodiments the transparent material includes polyester, polycarbonate, cellulosic, or cyclic polyolefins. In various embodiments, the transparent material is between 25 microns and 2 millimeters in thickness. In various embodiments the array comprises copper traces, and in some cases the copper traces are gold plated.

In various embodiments, the copper traces include space/trace dimensions varying from 5 microns by 5 microns to 500 microns by 500 microns in any combination of aforementioned dimensions. In various embodiments, the array utilizes one of 50 micron by 50 micron, 75 micron by 75 micron, or 100 micron by 100 micron space/trace dimensions.

Some exemplary embodiments include methods of forming a micro structured electrode array for measurement of living cells, comprising: forming an array of patterned electrodes on a substrate having space/trace dimensions varying from 5 microns by 5 microns to 500 microns by 500 microns in any combination of aforementioned dimensions; attaching the substrate to a microwell plate; and providing a connection to the array of patterned electrodes for use by a microcontroller such that the electrical characteristics of the array electrodes can be measured and monitored. In various embodiments the array is fabricated onto a printed circuit board. In various embodiments the printed circuit board is a transparent material. In various embodiments the transparent material includes polyester, polycarbonate, cellulosic, or cyclic polyolefins. In various embodiments the transparent material is between 25 microns and 2 millimeters in thickness. In various embodiments the method comprises using copper traces for the electrode array. In various embodiments the copper traces are gold plated. In various embodiments, the method includes utilizing one of 50 micron by 50 micron, 75 micron by 75 micron, or 100 micron by 100 micron space/trace dimensions. In various embodiments the array of patterned electrodes includes copper traces having space/trace dimensions varying from 5 microns by 5 microns to 500 microns by 500 microns in any combination of aforementioned dimensions. In various embodiments, the method further comprises loading cells into the microwells; and performing electrical measurement on a plurality of the microwells. In various embodiments the method includes measuring one or more of voltage, current, and resistance of each of the plurality of microwells; and determining electrical characteristic changes based on changes in the live cells. In various embodiments the method comprises using an array fabricated on a printed circuit board made of transparent material, wherein the array of patterned electrodes includes copper traces having space/trace dimensions varying from 5 microns by 5 microns to 500 microns by 500 microns; and comparing electrical characteristics of the plurality of microwells to that of a baseline electrical performance with growth media to demonstrate electrical characteristic changes based on cells growing in the plurality of microwells.

The above discussion is meant to be illustrative of the principle and various embodiments of the present subject matter. Numerous variations and modifications will become apparent to those skilled in the art once the above disclosure is fully appreciated. It is intended that the following claims be interpreted to embrace all such variations and modifications.

What is claimed is:

1. A method of forming a micro structured electrode array for measuring electrical characteristics of living cells, comprising:
    forming a projective capacitive sensing device including an array of patterned electrodes on a substrate, the patterned electrodes having trace width and spacing dimensions each varying from 5 microns to 500 microns;
    attaching the substrate to a microwell plate; and
    providing a connection between the array of patterned electrodes and a microcontroller configured to measure the electrical characteristics of the living cells when the living cells are attached to the patterned electrodes, the connection allowing for the measurement of the electrical characteristics of the living cells using the projective capacitive sensing device with the patterned electrodes arranged and connected in a self-capacitive configuration.

2. The method of claim 1, wherein the array is fabricated onto a printed circuit board.

3. The method of claim 2, wherein the printed circuit board is a transparent material.

4. The method of claim 3, wherein the transparent material includes polyester, polycarbonate, cellulosic, or cyclic polyolefins.

5. The method of claim 4, wherein the transparent material is between 25 microns and 2 millimeters in thickness.

6. The method of claim 1, comprising using copper traces for the electrode array.

7. The method of claim 6, wherein the copper traces are gold plated.

8. The method of claim 7, wherein the copper traces have trace width and spacing dimensions each being one of 50 micron, 75 micron, or 100 micron.

9. The method of claim 1, further comprising
    loading cells into the microwells; and
    performing electrical measurement on a plurality of the microwells.

10. The method of claim 9, further comprising:
    measuring one or more of voltage, current, and resistance of each of the plurality of microwells; and
    determining electrical characteristic changes based on changes in the live cells.

11. The method of claim 10, further comprising:
    using an array fabricated on a printed circuit board made of transparent material; and
    comparing electrical characteristics of the plurality of microwells to that of a baseline electrical performance with growth media to demonstrate electrical characteristic changes based on cells growing in the plurality of microwells.

* * * * *